United States Patent [19]

Byrd

[11] Patent Number: 5,448,985
[45] Date of Patent: Sep. 12, 1995

[54] ENDOTRACHEAL TUBE HOLDING DEVICE AND ASSOCIATED TUBE HOLDING METHOD

[76] Inventor: Timothy N. Byrd, 1267 Old Cades Cove Rd., Townsend, Tenn. 37882

[21] Appl. No.: 328,685

[22] Filed: Oct. 25, 1994

[51] Int. Cl.6 ............................................. A61M 16/00
[52] U.S. Cl. ...................... 128/207.17; 128/DIG. 26; 128/DIG. 15
[58] Field of Search .................. 128/207.17, DIG. 26, 128/DIG. 15

[56] References Cited

U.S. PATENT DOCUMENTS

| | | | |
|---|---|---|---|
| D. 310,721 | 9/1990 | Beisang | D24/49 |
| 3,046,989 | 7/1962 | Hill | 128/348 |
| 3,713,448 | 1/1973 | Arrott | 128/DIG. 26 |
| 3,826,254 | 7/1974 | Mellor | 128/133 |
| 3,927,676 | 12/1975 | Schultz | 128/351 |
| 3,977,407 | 8/1976 | Coleman et al. | 128/348 |
| 4,120,304 | 10/1978 | Moor | 128/348 |
| 4,142,527 | 3/1979 | Garcia | 128/348 |
| 4,249,529 | 2/1981 | Nestor et al. | 128/207.17 |
| 4,327,716 | 5/1982 | Ansted | 128/DIG. 26 |
| 4,333,468 | 6/1982 | Geist | 128/348 |
| 4,351,331 | 9/1982 | Gereg | 128/207.17 |
| 4,489,723 | 12/1984 | Simons et al. | 128/207.16 |
| 4,548,200 | 10/1985 | Wapner | 128/207.17 |
| 4,569,348 | 2/1986 | Hasslinger | 128/DIG. 15 |
| 4,583,976 | 4/1986 | Ferguson | 604/174 |
| 4,671,787 | 6/1987 | Widman | 128/DIG. 26 |
| 4,690,675 | 9/1987 | Katz | 604/177 |
| 4,744,358 | 5/1988 | McGinnis | 128/207.17 |
| 4,774,944 | 10/1988 | Mischinski | 128/207.17 |
| 4,799,923 | 1/1989 | Campbell | 128/DIG. 26 |
| 4,822,342 | 4/1989 | Brawner | 128/DIG. 26 |
| 4,823,789 | 4/1989 | Beisang | 128/207.18 |
| 4,836,200 | 6/1989 | Clark | 128/207.18 |
| 4,932,943 | 6/1990 | Nowak | 604/180 |
| 5,009,227 | 4/1991 | Nieuwstad | 128/207.17 |
| 5,037,397 | 8/1991 | Kalt et al. | 604/174 |
| 5,038,778 | 8/1991 | Lott | 128/207.17 |
| 5,042,477 | 8/1991 | Lewis | 128/207.17 |
| 5,135,506 | 8/1992 | Gentelia et al. | 128/DIG. 26 |
| 5,163,914 | 11/1992 | Abel | 128/DIG. 15 |
| 5,215,532 | 6/1993 | Atkinson | 604/180 |
| 5,306,233 | 4/1994 | Glover | 128/207.17 |

OTHER PUBLICATIONS

Brochure–Dale ® Endotracheal Tube Holder, ©1992, Rev. Sep. 1992.

Primary Examiner—Edgar S. Burr
Assistant Examiner—Aaron J. Lewis
Attorney, Agent, or Firm—Pitts & Brittian

[57] ABSTRACT

An endotracheal tube holding device for securing the position of an endotracheal tube. The tube holding device (10) includes first and second tube engaging apparatus (14, 16), each of which includes a foundation strap (24) having an outer bonding surface (30) proximate its distal end portion (26). Each of the tube engaging apparatus (14, 16) also includes a tube engaging strap (36) for releasably engaging and securing the position of the endotracheal tube (12). The tube engaging straps (36) each define a proximal end (38) secured to the operatively associated foundation strap (24) and an inner surface (42) coated with an adhesive for releasably engaging the outer bonding surface (30) of the operatively associated foundation strap (24). Also provided is a securing strap (18) having a first end portion for releasably engaging the proximal end portion of the foundation strap (24) of the first tube engaging apparatus (14) and a second end portion for releasably engaging the proximal end portion of the foundation strap (24) of the second tube engaging apparatus (16).

10 Claims, 4 Drawing Sheets

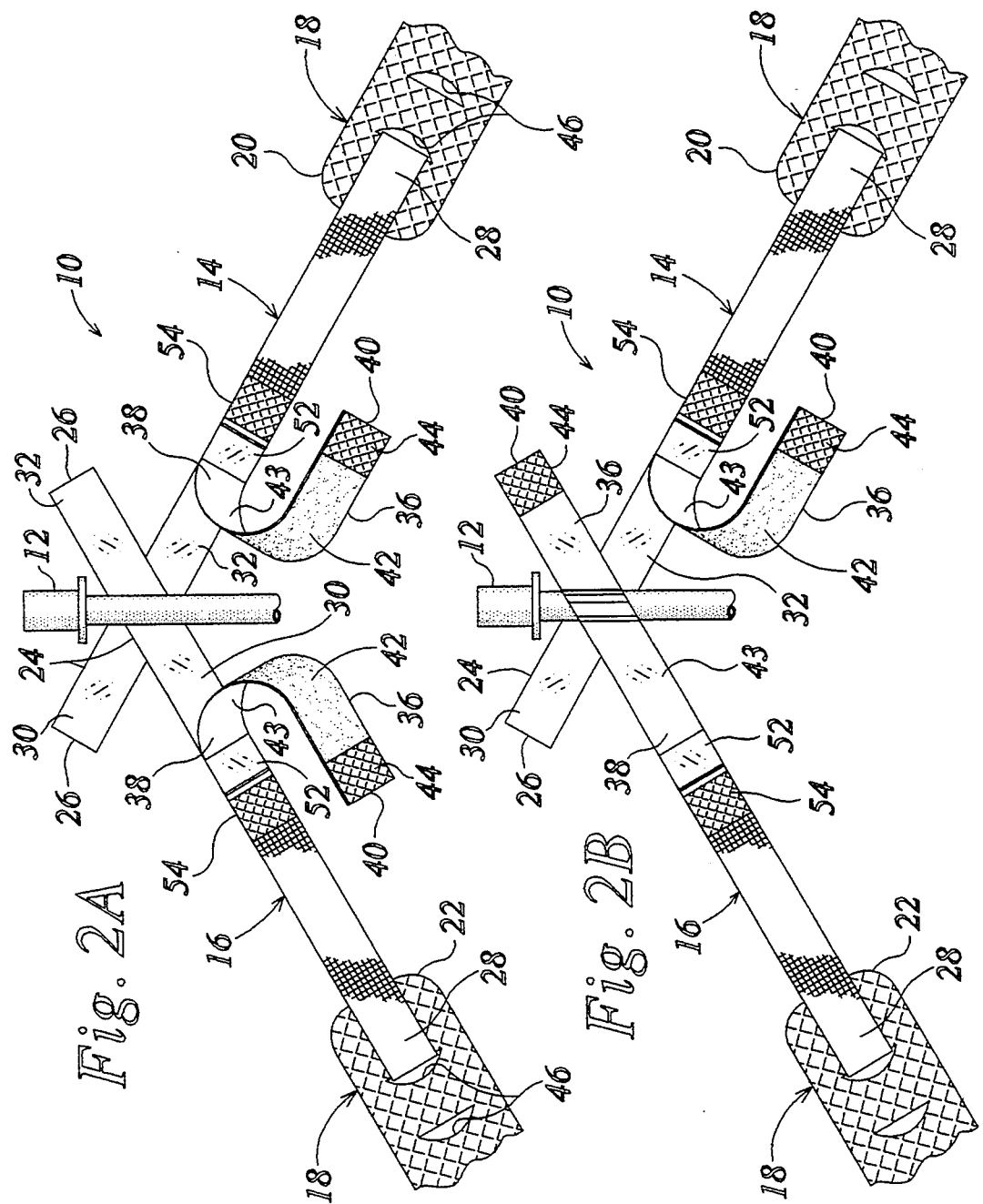

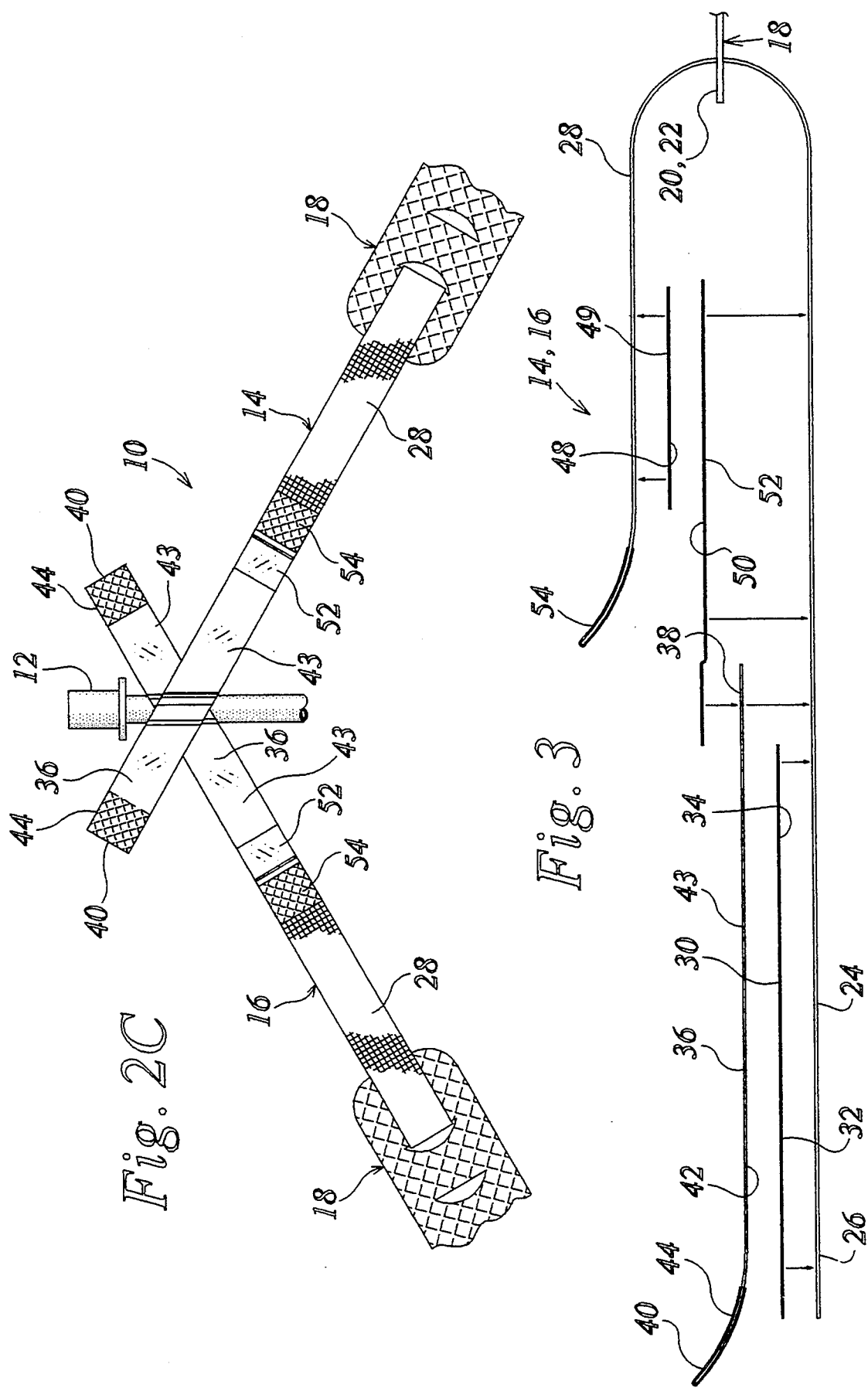

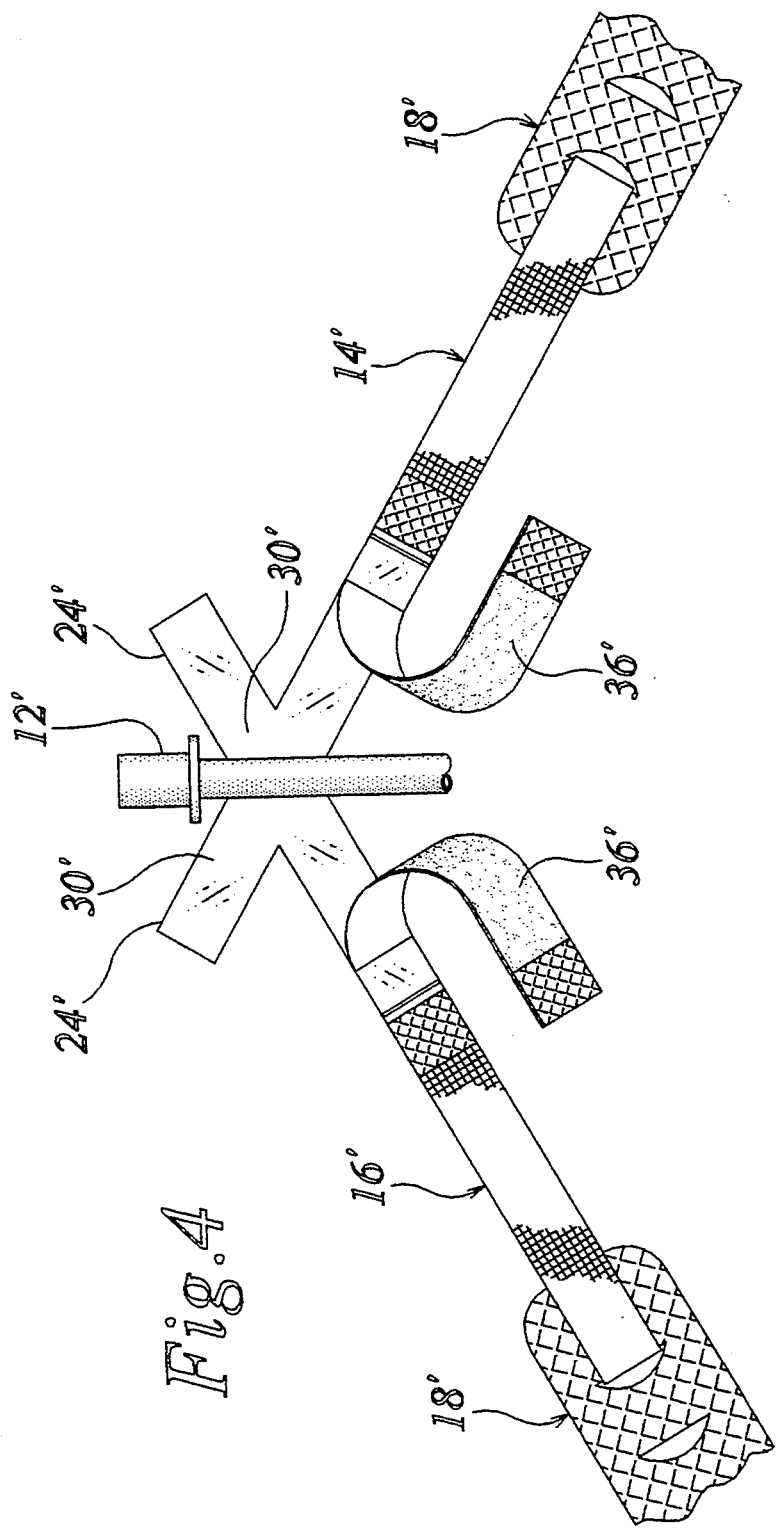

ENDOTRACHEAL TUBE HOLDING DEVICE AND ASSOCIATED TUBE HOLDING METHOD

TECHNICAL FIELD

This invention relates an endotracheal tube holding device for securing the position of a endotracheal tube as such tube is received through a nostril or the mouth of a patient. In this particular invention the tube holding device includes first and second tube engaging apparatus which engage the endotracheal tube proximate the point at which such tube enters the body of the patient.

BACKGROUND ART

The use of endotracheal tubes to effect artificial ventilation of a patient's lungs is a common medical procedure. Such tubes can be inserted through a nostril or mouth of a patient. However, once the endotracheal tube is inserted difficulties can arise in stabilizing the position of the tube such that it is not inadvertently removed and such that movement of the tube does not cause discomfort to the patient. Accordingly, attempts have been made to devise endotracheal tube holding devices which secure the position of the tube once it has been inserted. Certain examples of such devices are disclosed in U.S. Pat. Nos. 5,009,227; 4,774,944; 4,744,358; 4,489,723; 4,351,311; 4,249,529; and 3,927,676. Further, the Dale Endotracheal Tube Holder, manufactured by Dale Medical Products, Inc., of Plainville, Ma., is an example of such a device. However, the various holding devises have proven to be either ineffective for holding the tube in place, difficult to use, and/or expensive. Further, such devices are rarely suitable for use with both oral exiting tubes and nasal exiting tubes. Therefore, commonly the medical caretaker will improvise and use an adhesive tape method whereby a length of adhesive tape is wrapped around the patient's head, then split into two segments, and the segments are wrapped around the tube, with the remaining tape ends secured across the lip or over the nose of the patient. But, the adhesive tape rarely stays bonded to the skin or the tube for the desired length of time, particularly where silicone tubing is being utilized. In this regard, silicone is becoming the preferred fabricating material for endotracheal tubes, but adhesive tape does not bond well with the surface of a silicone tube.

Other tube holding devices are disclosed in U.S. Pat. Nos. 4,932,9434; 836,200; 5,037,397; 4,823,789; 3,046,989; Des. Pat. No. 310,721; 5,215,532; 4,690,675; 4,583,976; 4,333,468; 4,142,527; 4,120,304; 3,977,407; and 3,826,254.

Therefore, it is an object of the present invention to provide an endotracheal tube holding device for securing the position of a endotracheal tube.

It is another object of the present invention to provide an endotracheal tube holding device for securing the position of a endotracheal tube which utilizes friction and pressure to hold the endotracheal tube as well as adhesive surface bonding.

Yet another object of the present invention is to provide an endotracheal tube holding device for securing the position of a endotracheal tube which can be used with both orally exiting endotracheal tubes and nasal exiting endotracheal tubes.

Still another object of the present invention is to provide an endotracheal tube holding device for securing the position of a endotracheal tube which can be quickly and easily installed and allows subsequent adjustments of the position of the tube after initial installation.

Still another object of the present invention is to provide an endotracheal tube holding device for securing the position of a endotracheal tube which is inexpensive to manufacture such that it is economically disposable.

DISCLOSURE OF THE INVENTION

Other objects and advantages will be accomplished by the present invention which provides an endotracheal tube holding device for securing the position of an endotracheal tube. The tube holding device includes first and second tube engaging apparatus, each of which includes a foundation strap having an outer bonding surface proximate its distal end portion. Each of the tube engaging apparatus also includes a tube engaging strap for releasably engaging and securing the position of the endotracheal tube. The tube engaging straps define a proximal end secured to the operatively associated foundation strap and an inner surface coated with an adhesive for releasably engaging the outer bonding surface of the foundation strap with the endotracheal tube therebetween. Also provided is a securing strap having a first end portion for releasably engaging the proximal end portion of the foundation strap of the first tube engaging apparatus and a second end portion for releasably engaging the proximal end portion of the foundation strap of the second tube engaging apparatus.

In accordance with the method of the present invention the foundation strap of the first tube engaging apparatus is placed proximate the point at which the endotracheal tube enters the body of the patient. The foundation strap of the second tube engaging apparatus is then placed diagonally across the foundation strap of the first tube engaging apparatus, and the tube engaging straps are secured to the bonding surfaces of their operatively associated foundation straps with one engaging strap received over the other, and with the endotracheal tube disposed between the tube engaging straps and the foundation straps. Further, the securing strap is placed around the body of the patient, with its first end portion releasably engaging the proximal end portion of one foundation strap and its second end portion releasably engaging the proximal end portion of the other foundation strap, thereby facilitating the securing of the tube holding device on the body of the patient.

BRIEF DESCRIPTION OF THE DRAWINGS

The above mentioned features of the invention will be more clearly understood from the following detailed description of the invention read together with the drawings in which:

FIG. 2A illustrates a partial front elevation view of an endotracheal tube holding device of the present invention.

FIG. 2B illustrates a partial front elevation view of an endotracheal tube holding device of the present invention.

FIG. 2C illustrates a partial front elevation view of an endotracheal tube holding device of the present invention.

FIG. 3 illustrates an exploded plan view of a tube engaging apparatus of an endotracheal tube holding device of the present invention.

FIG. 4 illustrates a partial front elevation view of an alternate embodiment of an endotracheal tube holding device of the present invention.

BEST MODE FOR CARRYING OUT THE INVENTION

Figure 1:
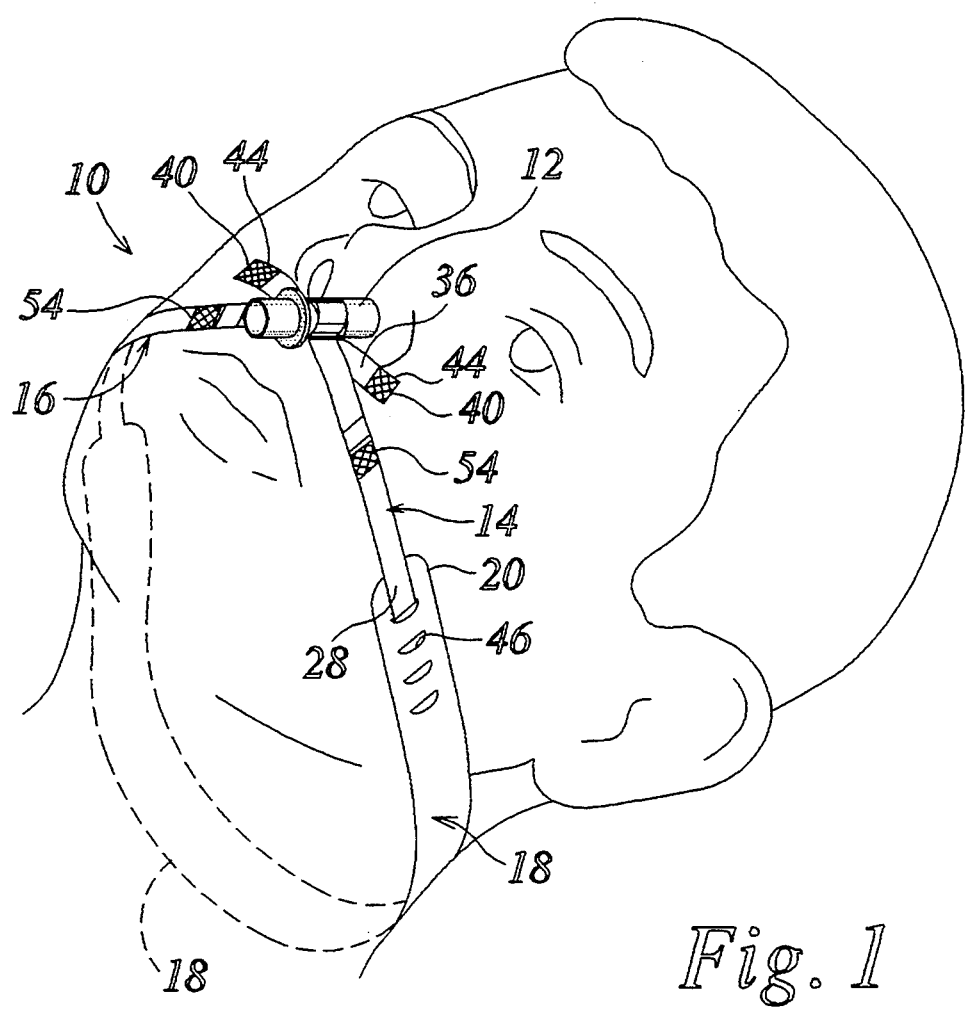
FIG. 1 illustrates perspective view of an endotracheal tube holding device of the present invention.

An endotracheal tube holding device incorporating various feature of the present invention is illustrated at 10 in the Figures. The device 10 is designed for securing the position of a endotracheal tube, such as the illustrated tube 12, as such tube is received through a nostril or the mouth of a patient. Whereas the device 10 is illustrated in FIG. 1 as being used to secure the position of an endotracheal tube 12 which is received through the nostril of a patient, it will be understood by those skilled in the art that the device 10 will serve to secure the position of endotracheal tubes which are inserted through the mouth of a patient as well.

The tube holding device 10 includes first and second tube engaging apparatus 14 and 16, respectively, for releasably engaging a tube 12, as the tube 12 is positioned in the nostril or mouth of a patient. As will be discussed further below, the tube engaging apparatus 14 and 16 are secured on the opposite end portions 20 and 22 of a securing strap 18 which is receive around the patients body proximate the head so as to hold the tube engaging apparatus 14 and 16 in place.

Each of the tube engaging apparatus 14 and 16 includes a flexible foundation strap 24 having a distal end portion 26 and a proximal end portion 28. Whereas in the preferred embodiment the foundation straps 24 are separately formed, it is anticipated that the foundation straps 24 can be integrally formed as illustrated at 24' in FIG. 4. Further, the straps 24 are preferably fabricated of a soft pliable material, such as a spun-bond polypropylene material which is soft, breathable, inexpensive, and comfortable to the patient. However, other suitable materials can be used if desired.

Each of the tube engaging apparatus 14 and 16 is provided with a smooth, substantially non-porous, outer bonding surface 30 proximate its distal end portion 26. As is best illustrated in FIG. 3, in the preferred embodiment a length of cellophane or plastic-backed adhesive tape 32 having an inner adhesive covered surface 34 (such as 3-M$^R$ 9921 bonding panel tape) is secured proximate the distal end portion 26 of the foundation strap 24 so as to provide the bonding surface 30.

Further, each of the tube engaging apparatus 14 and 16 also include a flexible tube engaging strap 36 for releasably engaging a tube 12. The tube engaging straps 36 define a proximal end 38 and a distal end 40. The proximal end 38 of the strap 36 is secured to the operatively associated foundation strap 24, with the strap 36 being positioned such that the interior surface 42 of the strap 36 is engagable with the bonding surface 30. In this regard, at least a substantial portion of the inner surface 42 of the tube engaging strap 36 is coated with an adhesive such that the strap 36 can be selectively secured to the bonding surface 30 of the foundation strap 24 with a tube 12 disposed therebetween, or with a tube 12 and a foundation strap 24 disposed therebetween. One suitable fabricating material for the straps 36 is 3-M$^R$ 9920 securing tape, but other suitable materials can be used if desired.

Thus, in securing an endotracheal tube 12 in accordance with the method of the present invention, the foundation strap 24 of the first tube engaging apparatus 14 is positioned between the tube 12 and the patient, with the foundation strap 24 of the second tube engaging apparatus 16 being positioned diagonally across the foundation strap 24 of the first engaging apparatus 14. (See FIG. 2A) The tube engaging straps 36 of the first and second tube engaging apparatus 14 and 16 are then releasably secured over the tube 12 so as to engage the tube 12 and the operatively associated bonding surface 30. (See FIG. 2B and 2C). Alternatively, a tube 12 can be secured by positioning the foundation strap 24 of the first tube engaging apparatus 14 between the tube 12 and the patient and positioning the operatively associated tube engaging strap 36 over the tube 12 and securing it to the foundation strap 24. The foundation strap 24 of the second tube engaging apparatus 16 is then positioned diagonally beneath the foundation strap 24 of the first tube engaging apparatus 14, and the tube engaging strap 36 of the second tube engaging apparatus 16 is positioned over the tube 12 and other strap 36 and secured to the foundation strap 24 of the second tube engaging apparatus 16.

Accordingly, the tube 12 is firmly secured between the diagonally crossing foundation straps 24 and diagonally crossing tube engaging straps 36. (See FIG. 20). However, the tube 12 can be quickly and easily released by pulling back the tube engaging straps 36. In this regard, each of the engaging straps 36 is provided with a smooth, substantially non-porous outer bonding surface 43 which is releasably receptive of the adhesive covered interior surface 42 of the other engaging strap 36. Thus, when the tube 12 is being released, the overlapping strap 36 will disengage from the underlying strap 36 without damage to the device 10. In the preferred embodiment the bonding surface 43 is defined by a length of cellophane or plastic-backed tape such as 3-M$^R$ 9921 bonding panel tape. Further, it will be noted that in the preferred embodiment the distal ends 40 of the tube engaging straps 36 carry tab members 44, each of which defines an area which is free of adhesive, and preferably of increased thickness, so as to facilitate the manipulation of the tube engaging straps 36.

As noted above, the securing strap 18 serves to secure the device 10 about the body of the patient proximate the head so as to maintain the position of the tube engaging apparatus 14 and 16, and, thus, the tube 12 engaged thereby. In this regard, in the preferred embodiment adjustable securing mechanisms are provided for securing the each of the tube engaging apparatus 14 and 16 to the opposite ends 20 and 22 of the securing strap 18 such that the length of the device 10 is adjustable to accommodate different patients.

More specifically, in the preferred embodiment of FIG. 3 the securing strap 18 is provided with selectively spaced openings 46 for selectively receiving therethrough the proximal end portions 28 of the tube engaging apparatus 14 and 16. Each of the proximal end portions 28 has an adhesive surface 48, which in the preferred embodiment is defined by a length of double sided adhesive tape 49, such as, for example, Flexcon H-566, 3 mil tape. Further, the foundation straps 24 are each provided with a smooth, substantially non-porous, outer bonding surface 50 to which the adhesive surface 48 can be releasably secured after the proximal end portion 28 has been received through an opening 46. In the preferred embodiment the bonding surfaces 50 are defined by lengths of plastic or cellophane tape 52, such as, for example, 3-M$^R$ 9921 bonding panel tape, which are secured to the foundation straps 24.

Thus, it will be recognized that by selecting the openings 46 to be used, and by selecting the position along the bonding surfaces 50 at which the adhesive surfaces 48 are secured, the effective length of the device 10 can be changed to accommodate different patients and to effect a tightening or loosening of the device 10 as it is positioned about a patient's body. It will be noted that the proximal end portions 28 of the foundation straps 24 can be provided with tab members 54 which define an area which is free of adhesive, and preferably of increased thickness, so as to facilitate the manipulation of the proximal end portions 28 and the adjustable securing of the tube engaging apparatus 14 and 16 to the securing strap 18. It will also be noted that in the preferred embodiment the length of tape 52 is of sufficient length to extend over the proximal end portion 38 of the operatively associated tube engaging strap 36 such that it serves to secure the strap 36 to the foundation strap 24.

In the preferred embodiment the securing strap 18 is fabricated of a spun-bond polypropylene material which is soft, breathable, inexpensive, and comfortable to the patient. However, other suitable materials can be used if desired.

In light of the above it will be recognized that the present invention provides an endotracheal tube holding device and an associated method having great advantages over the prior art. In this regard, the endotracheal tube holding device 10 secures the position of a endotracheal tube not only through adhesive surface bonding, but through friction and pressure as the tube is positioned between the foundation straps and tube engaging straps. Accordingly, if the adhesive bond fails the tube remains securely positioned in the device 10. The endotracheal tube holding device 10 can be used with both orally exiting endotracheal tubes and nasal exiting endotracheal tubes, and can be quickly and easily installed. Moreover, the device 10 allows subsequent adjustments of the position of the tube after initial installation. It will also be noted that the holder is extremely thin, strong and durable, and the entire device can be quickly washed, dried and reinstalled, yet can be inexpensively manufactured so as to be economically disposable.

While a preferred embodiment has been shown and described, it will be understood that there is no intent to limit the invention to such disclosure, but rather it is intended to cover all modifications and alternate constructions falling within the spirit and scope of the invention as defined in the appended claims.

I claim:

1. An endotracheal tube holding device for securing the position of an endotracheal tube, said tube holding device comprising:
   a first tube engaging apparatus for releasably engaging the endotracheal tube, said first tube engaging apparatus including a first foundation strap having a distal end portion and an outer bonding surface proximate said distal end portion, said first tube engaging apparatus having a first tube engaging strap for releasably engaging and securing the position of the endotracheal tube, said first tube engaging strap defining a proximal end secured to said first foundation strap and an inner surface, at least a portion of which is coated with an adhesive for releasably engaging said outer bonding surface; and
   a second tube engaging apparatus for releasably engaging the endotracheal tube, said second tube engaging apparatus including a second foundation strap having a distal end portion and a further outer bonding surface proximate said distal end portion of said second foundation strap, said second tube engaging apparatus having a second tube engaging strap for releasably engaging and securing the position of the endotracheal tube, said second tube engaging strap defining a proximal end secured to said second foundation strap and an inner surface, at least a portion of which is coated with an adhesive for releasably engaging said further outer bonding surface with the endotracheal tube therebetween.

2. The endotracheal tube holding device of claim 1 wherein said outer bonding surface of said first foundation strap and said further outer bonding surface of said second foundation strap define smooth, substantially non-porous surfaces to facilitate repetitive engagement of said first tube engaging strap with said outer bonding surface and repetitive engagement of said second tube engaging strap with said further outer bonding surface.

3. The endotracheal tube holding device of claim 2 wherein said first tube engaging strap includes a smooth, substantially non-porous further outer bonding surface for releasably engaging said inner surface of said second tube engaging strap and wherein said second tube engaging strap includes a smooth, substantially non-porous further outer bonding surface for releasably engaging said inner surface of said first tube engaging strap.

4. The endotracheal tube holding device of claim 3 wherein said tube holding device further comprises a securing strap having first and second opposite end portions, and wherein said first foundation strap defines a proximal end portion secured to said first end portion of said securing strap and said second foundation strap defines a proximal end portion secured to said second end portion of said securing strap, whereby said securing strap is received about the body of a patient to facilitate the securing of said tube holding device on the body of the patient.

5. The endotracheal tube holding device of claim 4 wherein said tube holding device includes a mechanism for adjustably securing said proximal end portion of said first foundation strap to said first end portion of said securing strap and includes a further mechanism for adjustably securing said proximate end portion of said second foundation strap to said second end portion of said securing strap, whereby the length of said tube holding device can be altered to accommodate different patients and to tighten and loosen said tube holding device as it is positioned on the patient.

6. The endotracheal tube holding device of claim 4 wherein said first end portion of said securing strap includes a plurality of selectively spaced openings for receiving said proximal end portion of said foundation strap therethrough, and said second end portion of said securing strap includes a plurality of selectively spaced further openings for receiving said proximal end portion of said second foundation strap therethrough, and wherein said first foundation strap is provided with a first adhesive surface portion for releasably engaging said first foundation strap along a first bonding surface selectively spaced from said first adhesive surface portion whereby said first foundation strap is releasably secured to said first end portion of said securing strap, said second foundation strap is provided with a second adhesive surface portion for releasably engaging said second foundation strap along a second bonding surface provided on said second foundation strap selectively spaced from said second adhesive surface portion whereby said second foundation strap is releasably secured to said second end portion of said securing strap.

7. An endotracheal tube holding device for securing the position of an endotracheal tube, said tube holding device comprising:
  a first tube engaging apparatus for releasably engaging the endotracheal tube, said first tube engaging apparatus including a first foundation strap having a distal end portion and a proximal end portion and having a smooth, substantially non-porous outer bonding surface proximate said distal end portion, said first tube engaging apparatus including a first tube engaging strap for releasably engaging and securing the position of the endotracheal tube, said first tube engaging strap defining a proximal end secured to said first foundation strap and an inner surface, at least a portion of which is coated with an adhesive for releasably engaging said outer bonding surface;
  a second tube engaging apparatus for releasably engaging the endotracheal tube, said second tube engaging apparatus including a second foundation strap for being received over said first foundation strap, said second foundation strap having a distal end portion and a proximal end portion, and having a smooth, substantially non-porous further outer bonding surface proximate said distal end portion of said second foundation strap, said second tube engaging apparatus having a second tube engaging strap for releasably engaging and securing the position of the endotracheal tube, said second tube engaging strap defining a proximal end secured to said second foundation strap and an inner surface, at least a portion of which is coated with an adhesive for releasably engaging said further outer bonding surface with the endotracheal tube and said first foundation strap therebetween; and
  a securing strap having a first end portion for releasably engaging said proximal end portion of said first foundation strap and a second end portion for releasably engaging said proximal end portion of said second foundation strap, whereby said securing strap is received about the body of a patient to facilitate the securing of said tube holding device on the body of the patient.

8. A method for securing the position of an endotracheal tube proximate the point at which the tube enters the body of a patient, said method comprising the steps of:
  placing a first foundation strap proximate the point at which the endotracheal tube enters the body of the patient;
  placing a second foundation strap diagonally across said first foundation strap;
  securing a first tube engaging strap to said first foundation strap with the endotracheal tube therebetween, said first tube engaging strap having a proximal end secured to said first foundation strap and an inner adhesive surface for engaging said first foundation strap; and
  securing a second tube engaging strap to said second foundation strap with the endotracheal tube therebetween, said first tube engaging strap having a proximal end secured to said first foundation strap and a inner adhesive surface for engaging said second foundation strap.

9. The method for securing the position of an endotracheal tube of claim 8 comprising the further step of placing a securing strap around the body of the patient, said securing strap having a first end portion releasably engaging a proximal end portion of said first foundation strap and a second end portion releasably engaging a proximal end portion of said second foundation strap, whereby said securing strap is received about the body of a patient to facilitate the securing of said tube holding device on the body of the patient.

10. A method for securing the position of an endotracheal tube proximate the point at which the tue enters the body of a patient, said method comprising the steps of:
  placing a first foundation strap proximate the point at which the endotracheal tube enters the body of the patient;
  securing a first tube engaging strap to said first foundation strap with the endotracheal tube therebetween, said first tube engaging strap having a proximal end secured to said first foundation strap and an inner adhesive surface for engaging said first foundation strap;
  placing a second foundation strap diagonally across said first foundation strap; and
  securing a second tube engaging strap to said second foundation strap with the endotracheal tube and said first engaging strap therebetween, said second tube engaging strap having a proximal end secured to said first foundation strap and a inner adhesive surface for engaging said second foundation strap.

* * * * *